United States Patent [19]

Spavins

[11] Patent Number: 4,855,500
[45] Date of Patent: Aug. 8, 1989

[54] PROCESS FOR PREPARING A KETIMINE

[75] Inventor: James C. Spavins, North Stonington, Conn.

[73] Assignee: Pfizer Inc., New York, N.Y.

[21] Appl. No.: 190,300

[22] Filed: May 4, 1988

[51] Int. Cl.$^4$ .......................................... C07C 119/14
[52] U.S. Cl. .................................................. 564/270
[58] Field of Search ............................... 564/270, 271

[56] References Cited

U.S. PATENT DOCUMENTS 4,536,518  8/1985  Welch, Jr. et al. ................. 514/647

OTHER PUBLICATIONS

W. M. Welch, Jr. et al., Journal of Medicinal Chemistry, vol. 27, No. 11, p. 1508 (1984).
E. P. Kyba in Organic Preparations and Procedures, vol. 2(2), p. 149 (1970).
K. Taguchi et al., in the Journal of Organic Chemistry, vol. 26, p. 1570 (1971).

Primary Examiner—James H. Reamer
Attorney, Agent, or Firm—Peter C. Richardson; Paul H. Ginsburg; Lawrence C. Akers

[57] ABSTRACT

An improved condensation process for preparing N-[4-(3,4-dichlorophenyl)-3,4-dihydro-1(2H)-naphthalenylidene]methanamine from 4-(3,4-dichlorophenyl)-3,4-dihydro-1(2H)-naphthalenone and methylamine is disclosed. The process involves the use of a hydratable molecular sieve having a pore size that is at least about three Angstrom units in diameter as the dehydrating agent (catalyst) in a reaction-inert aprotic organic solvent. The ketimine final product so produced is known to be useful as an intermediate leading to cis-(1S)(4S)-N-methyl-4-(3,4-dichlorophenyl)-1,2,3,4-tetrahydro-1-naphthalena ine (sertraline), which is an anti-depressant agent.

12 Claims, No Drawings

PROCESS FOR PREPARING A KETIMINE

BACKGROUND OF THE INVENTION

This invention relates to a new and useful process for preparing a known ketimine compound. More particularly, it is concerned with an improved method for preparing N-[4-(3,4-dichlorphenyl)-3,4-dihydro-1(2H)-naphthalenylidene]methanamine, which is known to be of value as a key intermediate in the production of the antidepressant agent known as cis-(1S)(4S)-N-methyl-4-(3,4-dichlorophenyl)-1,2,3,4-tetrahydro-1-naphthalenamine (sertraline).

In the past, N-[4-(3,4-dichlorophenyl)-3,4-dihydro-1(2H)-naphthalenylidene]methanamine has been obtained by condensing 4-(3,4-dichlorophenyl)-3,4-dihydro-1(2H)-naphthalenone with methylamine in the presence of titanium tetrachloride in accordance with the method described by W. R. Welch, Jr. et al. in U.S. Pat. No. 4,536,518, as well as in the paper of the same authors appearing in the *Journal of Medicinal Chemistry* Vol. 27, No. 11, p. 1508 (1984). However this, method involves the use of certain stringent safety requirements that are called for in connection with the handling of titanium tetrachloride (necessitated by the fact that this reagent is extremely reactive with water) and the use of various hazardous waste disposal techniques that are required for the removal of the titanium tetrachloride by-products of the condensation reaction (viz., titanium dioxide and methylamine hydrochloride). In the search for newer and more improved methods of production in this particular area, little is known about the use of other dehydrating agents, such as molecular sieves, etc., with the naphthalenone ring system in this type condensation reaction even though these agents have been employed in the past with variable success in the field of condensation chemistry (i.e., ketimine synthesis) with respect to other ketone substrates. For instance, E. P. Kyba in *Organic Preparations and Procedures*, Vol. 2(2), p. 149 (1970) discloses the use of molecular sieves to prepare several ketimines derived from various methyl ketones and methylamine, while K. Taguchi et al, in the *Journal of Organic Chemistry*, Vol. 36, p. 1570 (1971) extends this work to certain hindered ketones and further reports on the catalytic effects of molecular sieves in the formation of ketimines derived from medium-sized ring ketones and aromatic amines such as aniline and m-toluidine.

SUMMARY OF THE INVENTION

In the accordance with the present invention, there is now provided for the first time an improved process for preparing N-[4-(3,4-dichlorophenyl)-3,4-dihydro-1(2H)-naphthalenylidene]methanamine, known to be useful as an intermediate as hereinbefore discussed, by a novel method which involves condensing 4-(3,4-dichlorophenyl)-3,4-dichloro-1(2H)-naphthalenone with methylamine in the presence of a hydratable molecular sieve as catalyst, whereby water is effectively removed by the catalyst and the desired ketimine final product is readily obtained in pure form and in high yield. More particularly, the novel one-step process of the invention involves contacting 4-(3,4-dichlorophenyl)-3,4-dihydro-1(2H)-naphthalenone with methylamine in a reaction-inert aprotic organic solvent in the presence of a hydratable molecular sieve having a pore size of at least about three Angstrom units in diameter, whereby water is removed from the resultant reaction mixture until formation of the desired ketimine final product is substantially complete. In this way, 4-(3,4-dichlorophenyl)-3,4-dihydro-1(2H)-naphthalenone is converted to N-[4-(3,4-dichlorophenyl)-3,4-dihydro-1(2H)-naphthalenylidene]methanamine in a most facile manner without the previously discussed disadvantages connected with the use of titanium tetrachloride. As previously indicated, the latter-named final product is known to be useful as a valuable intermediate in the production of the antidepressant agent known as sertraline, which is cis-(1S)-(4S)-N-methyl-4-(3,4-dichlorphenyl)-1,2,3,4-tetrahydro-1-naphthalenamine see U.S. Pat. No. 4,536,518 as well as the *Journal of Medicinal Chemistry*, Vol. 27, No. 11, p. 1508 (1984)].

DETAILED DESCRIPTION OF THE INVENTION

In accordance with the process of this invention, the reaction is generally carried out by using an excess in moles of methylamine with respect to the 4-(3,4-dichlorophenyl)-3,4-dihydro-1(2H)-naphthalenone starting material and preferably by using at least about ten moles of amine per one mole of starting material, with the most preferred range being from about 10:1 to about 20:1, in order to effect the desired condensation (or iminolysis) at the 1-position of the molecule. The process is normally conducted in a reaction-inert aprotic organic solvent containing the hydratable molecule sieve as catalyst at a temperature that is in the range of from about 20° C. up to about 100° C., and preferably at a temperature that is in the range of from about 35° C. up to about 80° C., at a pressure ranging from about one to about ten atmospheres until the reaction t form the desired ketimine is substantially complete (this will generally require a period of at least about two hours). Preferred reaction-inert aprotic organic solvents for use in this connection include lower dialkyl ethers such as diethyl ether, di-isopropyl ether and di-n-butyl ether, cyclic ethers such as tetrahydrofuran and dioxane, aromatic hydrocarbons such as benzene, toluene and xylene and chlorinated lower hydrocarbons such as methylene chloride, ethylene dichloride, s-tetrachlorethane, chloroform and carbon tetrachloride. Preferred molecular sieves employed as catalysts for these purposes will generally include those having a pore size that is in the range of from about three to about ten Angstroms units in diameter, with the most preferred having a pore size that is about five Angstrom units in diameter. In practice, the reaction is most conveniently carried out in a standard pressure reactor, with the spent molecular sieves being removed during the course of the reaction and replaced with a fresh charge of catalyst if so desired. Upon completion of the reaction, the desired product, viz., N-[4-(3,4-dichlorophenyl)-3,4-dihydro-1(2H)-naphthalenylidene]methanamine, is readily recovered from the reaction mixture by any number of standard means and preferably, by first removing the catalyst by means of filtration and thereafter the solvent by means by evaporation under reduced pressure, etc. or else by replacement of the solvent with a higher boiling solvent (e.g., hexane for methylene chloride) from which the desired product can readily precipitate in pure crystalline form.

The 4-(3,4-dichlorophenyl)-3,4-dihydro-1(2H)-naphthalenone starting material required for conducting the process of this invention is a known compound which can easily be synthesized by those skilled in the art starting from common chemical reagents and using conventional methods of organic synthesis. For instance, this particular compound is readily prepared by employing the method W. M. Welch, Jr. et al., as described in U.S. Pat. No. 4,536,518 or the *Journal of Medicinal Chemistry*, Vol. 27, No. 11, p. 1508 (1984).

The hydratable molecular sieves employed as catalysts or as dehydrating agents in the process of this invention are commercially available materials well-known to those skilled in the art. In general, the term "molecular sieve" refers to a group of adsorptive desiccants which are crystalline alumino-silicate materials, chemically similar to clays and feldspars and belonging to a class of minerals known as zeolites. For instance, molecular sieve Type No. 4A (Linde) is of the formula $Na_{12}[(AlO_2)_{12}(SiO_2)_{12}]$, while molecular sieve Type No. 13X (Linde) is of the formula $Na_{86}[(AlO_2)_{86}(SiO_2)_{106}]$. These particular white crystalline powders are all generally of 1-5 micron particle size. The outstanding characteristic of these materials is their ability to undergo dehydration with little or no change in crystal structure. The dehydrated crystals are interlaced with regularly spaced channels of molecular dimensions. This network of uniform pores comprises almost 50% of the total volume of the crystals. Molecular sieves have a strong tendency to readsorb water and hence, are easily hydratable providing their pore size is large enough to permit water molecules to enter in and pass through the pore of the crystal (and hence, enter into the crystal cavities of the lattice network).

As a result, the hydratable sieves of the present invention must preferably exhibit a pore size that is at least about three Angstrom units in diameter. These materials are available commercially from the Davison Chemical Company (Fisher Scientific Co.) of Baltimore, Md. or from the Linde Company, a division of the Union Carbide Corporation of Danbury, Conn. For example, molecular sieve Type No. 3A (Linde) will adsorb molecules of less than three Angstrom units in diameter (includes water), while Type No. 4A will adsorb molecules of less than four Angstroms units in diameter and Type No. 5A will adsorb molecules of less than five Angstrom units in diameter, with both Type Nos. 10X and 13X adsorbing molecules of ten Angstrom units in diameter or less, etc.

As previously indicated, the N-[4-(3,4-dichlorophenyl)-3,4-dihydro-1(2H)-naphthalenylidene]methanamine final product afforded by the process of this invention is a valuable intermediate that ultimately leads to the antidepressant agent known as sertraline or cis-(1S)(4S)-N-methyl-4-(3,4-dichlorophenyl)-1,2,3,4-tetrahydro-1-naphthaleneamine as disclosed in the previously discussed prior art. More specifically, N-[4-(3,4-dichlorophenyl)-3,4-dihydro-1(2H)-naphthalenylidene]methanamine is first converted to racemic cis-N-methyl-4-(3,4-dichlorophenyl)-1,2,3,4-tetrahydro-1-naphthalenamine prior to ultimately yielding the desired cis- (1S)(4S)-N-methyl-4-(3,4-dichlorophenyl)-1,2,3,4-tetrahydro-1-naphthalenamine by the facile step-wise method of the art process as earlier described by W. M. Welch, Jr. et al. in U.S. Pat. No. 4,536,518 and in the *Journal of Medicinal Chemistry*, Vol. 27, No. 11, p. 1508 (1984).

Hence, the novel process of the present invention now provides the required and valuable N-[4-(3,4-dichlorophenyl)-3,4-dihydro-1(2H)-naphthalenylidene]methanamine discussed above in pure form and in high yield by a unique one-step method, which represents a major improvement in the view of the ease of synthesis and greatly reduced nature of the costs involved. More specifically, it circumvents the use of titanium tetrachloride as a catalyst with its associated potential hazards and allows the reaction to proceed under milder and more economical conditions, particularly since the molecular sieves employed as catalyst can easily be recovered from the reaction mixture and then regenerated to yield a fresh charge of hydratable (i.e., activated) material.

EXAMPLE 1

In a pressure reactor, there were placed 30 g. (0.103 mole) of 4-(3,4-dichlorophenyl)-3,4-dihydro-1(2H)-naphthalenone (prepared according to the procedure described by W. M. Welch, Jr. et al. in U.S. Pat. No. 4,536,518) and 38.9 g. (1.22 mole) of anhydrous methylamine (condensed at 0° C.) in 350 ml. of methylene chloride at −12° C. To the resulting mixture, there were then added 18.6 g. of powdered molecular sieves (activated) Type No. 5A (Linde). The charged reactor was then heated to 50° C. (the recorded pressure was 16 p.s.i.g.) and the reaction mixture shaken at that point for a period of four hours. At the end of this time, (the recorded pressure was now 8 p.s.i.g.), the reactor was cooled, vented and the spent molecular sieves were subsequently removed from the mixture by means of filtration. Thereafter, 18.6 g. of fresh molecular sieves were charged to the reactor together with an additional 17.2 g. (0.55 mole) of anhydrous methylamine, and the reactor and its contents were again heated to 50° C. This procedure was continued until gas chromatographic analysis indicated a 96% conversion to the desired ketimine (total time required was ca. 24 hours). Upon completion of the reaction, the spent molecular sieves were removed by filtration and the methylene chloride solvent was displaced with 500 ml. of hexane from which the desired product soon crystallized in pure form. In this manner, there was ultimately obtained 27.2 g. (87%) of pure N-[4-(3,4-dichlorophenyl)-3,4-dihydro-1(2H)-naphthalenylidene]methanamine (m.p. 145°-146° C.). The pure product was identical in every respect with the product reported by W. M. Welch, Jr. et al., in U.S. Pat. No. 4,536,518, as particularly attested to by nuclear magnetic resonance data.

EXAMPLE 2

The procedure described in Example 1 is repeated except that toluene is the solvent employed in lieu of methylene chloride and substantially the same results are achieved. In this particular case, the final product obtained, viz., N-[4-(3,4-dichlorophenyl)-3,4-dihydro-1(2H)-naphthalenylidene]methanamine, is identical in every respect with the product of Example 1.

EXAMPLE 3

The procedure described in Example 1 is repeated except that tetrahydrofuran is the solvent employed in lieu of methylene chloride and substantially the same results are achieved. In this particular case, the final product obtained, viz., N-[4-(3,4-dichlorophenyl)-3,4-dihydro-1(2H)-naphthalenylidene]methanamine, is identical in every respect with the product of Example 1.

EXAMPLE 4

The procedure described in Example 1 is repeated except that the hydratable molecular sieve employed as catalyst is powdered molecular sieve Type No. 3A (Linde) rather than Type 5A and substantially the same results are achieved. In this particular case, the final product obtained, viz., N-[4-(3,4-dichlorophenyl)-3,4-dihydro-1(2H)-naphthalenylidene]methanamine is identical in every respect with the product of Example 1.

EXAMPLE 5

The procedure described in Example 1 is repeated except that the hydratable molecular sieve employed as catalyst is powdered molecular sieve Type No. 4A (Linde) rather than Type 5A and substantially the same results are achieved. In this particular case, the final product obtained, viz., N-[4-(3,4-dichlorophenyl)-3,4-dihydro-1(2H)-naphthalenylidene]methanamine is identical in every respect with the product of Example 1.

EXAMPLE 6

The procedure described in Example 1 is repeated except that the hydratable molecular sieve employed as catalyst is powdered molecular sieve Type No. 10X (Linde) rather than Type 5A and substantially the same results are achieved. In this particular case, the final product obtained, viz., N-[4-(3,4-dichlorophenyl)-3,4-dihydro-1(2H)-naphthalenylidene]methanamine is identical in every respect with the product of Example 1.

I claim:

1. A process for preparing N-[4-(3,4-dichlorophenyl)-3,4-dihydro-1(2H)-naphthalenylidene]methanamine, which comprises contacting 4-(3,4-dichlorophenyl)-3,4-dihydro-1(2H)-naphthalenone with methylamine in a reaction-inert aprotic organic solvent in the presence of a hydratable molecular sieve having a pore size that is at least about three Angstrom units in diameter as catalyst, whereby water is removed from the resultant reaction mixture until formation of the desired ketimine final product is substantially complete.

2. A process as claimed in claim 1 wherein the reaction is carried out by using an excess in moles of methylamine with respect to the 4-(3,4-dichlorophenyl)-3,4-dihydro-1(2H)-naphthalenone starting material.

3. A process as claimed in claim 1 wherein the reaction is conducted at a temperature that is in the range of from about 20° C. up to about 100° C. at a pressure ranging from about one to about ten atmospheres.

4. A process as claimed in claim 1 wherein the aprotic organic solvent employed is tetrahydrofuran.

5. A process as claimed in claim 1 wherein the aprotic organic solvent employed is toluene.

6. A process as claimed in claim 1 wherein the aprotic organic solvent employed is methylene chloride.

7. A process in claim 1 wherein the hydratable molecular sieve employed as catalyst has a pore size that is in the range of from about three to about ten Angstrom units in diameter.

8. A process as claimed in claim 7 wherein the hydratable molecular sieve employed as catalyst has a pore size that is about three Angstrom units in diameter.

9. A process as claimed in claim 7 wherein the hydratable molecular sieve employed as catalyst has a pore size that is about four Angstrom units in diameter.

10. A process as claimed in claim 7 wherein the hydratable molecular sieve employed as catalyst has a pore size that is about five Angstrom units in diameter.

11. A process as claimed in claim 1 wherein the hydratable molecular sieve employed as catalyst has a pore size that is about ten Angstrom units in diameter.

12. A process as claimed in claim 1 wherein the N-[4-(3,4-dichlorophenyl)-3,4-dihydro-1(2H)-naphthalenylidene]methanamine so produced is recovered from the reaction mixture.

* * * * *